(12) United States Patent
Bullister

(10) Patent No.: US 6,697,055 B1
(45) Date of Patent: *Feb. 24, 2004

(54) MULTIFUNCTIONAL PORTABLE COMPUTING DEVICE WITH SPECIAL HOUSING

(76) Inventor: Edward Bullister, 20 Rolling La., Weston, MA (US) 02493

(*) Notice: Subject to any disclaimer, the term of this patent is extended or adjusted under 35 U.S.C. 154(b) by 0 days.

This patent is subject to a terminal disclaimer.

(21) Appl. No.: 09/716,754

(22) Filed: Nov. 20, 2000

Related U.S. Application Data

(62) Division of application No. 09/122,677, filed on Jul. 27, 1998, now Pat. No. 5,996,796, which is a division of application No. 08/558,688, filed on Nov. 16, 1995, now abandoned.

(51) Int. Cl.[7] ................................................ G09G 5/00
(52) U.S. Cl. ........................ 345/168; 400/680; 400/682; 361/680
(58) Field of Search ................................ 345/168, 169, 345/166; 400/680, 682, 691, 692, 693; 361/679, 680, 681, 683

(56) References Cited

U.S. PATENT DOCUMENTS

| | | | |
|---|---|---|---|
| 3,622,720 A | 11/1971 | Allen | 200/50 A |
| 3,940,758 A | 2/1976 | Margolin | 340/337 |
| 4,075,702 A | 2/1978 | Davies | 364/705 |
| 4,264,962 A | 4/1981 | Kodaira | 364/707 |
| 4,395,704 A | 7/1983 | Kishimoto et al. | 340/365 |
| 4,517,660 A | 5/1985 | Fushimoto et al. | 364/708 |
| 4,597,681 A | 7/1986 | Hodges | 400/488 |
| 4,703,160 A | 10/1987 | Narishima et al. | 235/1 |
| 4,742,478 A | 5/1988 | Nigro | 364/708 |
| 4,796,977 A | 1/1989 | Drake | 350/331 |
| 4,799,771 A | 1/1989 | Taniguchi | 350/334 |
| 4,882,471 A | 11/1989 | Kai | 235/1 |
| 4,903,221 A | 2/1990 | Krenz | 364/708 |
| 4,918,632 A | 4/1990 | York | 364/708 |
| 4,926,365 A | 5/1990 | Hsieh | 364/708 |
| 4,939,514 A | 7/1990 | Miyazaki | 341/22 |
| 4,959,887 A | 10/1990 | Gruenberg et al. | 16/223 |
| 4,969,830 A | 11/1990 | Daly | 439/136 |
| 5,002,184 A | 3/1991 | Lloyd | 206/305 |
| 5,021,922 A | 6/1991 | Davis et al. | 361/380 |
| 5,067,834 A | 11/1991 | Szmanda | 400/489 |
| 5,087,910 A | 2/1992 | Guyot-Sionnest | 340/711 |
| 5,103,376 A | 4/1992 | Blonder | 361/393 |
| 5,109,354 A | 4/1992 | Yamashita | 364/708 |
| 5,119,078 A | 6/1992 | Grant | 340/711 |
| 5,122,876 A | 6/1992 | Aoki | 358/133 |
| 5,163,765 A | 11/1992 | Levy | 400/492 |
| 5,187,644 A * | 2/1993 | Crisan | 361/393 |
| 5,196,993 A | 3/1993 | Herron | 361/393 |
| 5,233,502 A | 8/1993 | Beatty | 361/729 |
| 5,235,495 A | 8/1993 | Blair et al. | 361/680 |
| 5,241,451 A | 8/1993 | Walburn | 361/785 |
| 5,260,885 A | 11/1993 | Ma | 364/708.1 |

(List continued on next page.)

FOREIGN PATENT DOCUMENTS

EP 0530829 A2 4/1992 ............. G06F/1/16

OTHER PUBLICATIONS

IBM Technical Disclosure Bulletin vol. 32, No. 10B, Mar. 1990 "Foldable Keyboard" marketing material.

*Primary Examiner*—Dennis-Doon Chow

(57) ABSTRACT

A portable computing device includes pivoting and hinging mechanisms which enable its housing to reconfigure to function in multiple modes. In one configuration the device functions as a laptop computer with keyboard input. In another configuration the device folds into a compact, handheld, pen-based computer. In another configuration the device folds around the display for protection during transport. A set of adjustable stops enable easy and repeatable transitions between the different configurations.

5 Claims, 13 Drawing Sheets

U.S. PATENT DOCUMENTS

| | | | |
|---|---|---|---|
| 5,267,127 A | 11/1993 | Pollitt | 361/680 |
| 5,268,817 A | 12/1993 | Miyagawa | 361/729 |
| 5,278,779 A * | 1/1994 | Conway et al. | 364/708 |
| 5,285,398 A | 2/1994 | Janik | 364/708.1 |
| 5,295,089 A | 3/1994 | Ambasz | 364/708.1 |
| 5,321,579 A | 6/1994 | Brown et al. | 361/681 |
| 5,325,984 A | 7/1994 | Ady et al. | 220/342 |
| 5,333,116 A | 7/1994 | Hawkins et al. | 364/708.1 |
| 5,335,142 A | 8/1994 | Anderson | 361/681 |
| 5,340,073 A | 8/1994 | Masakazu | 248/291 |
| 5,345,362 A | 9/1994 | Winkler | 361/681 |
| 5,347,477 A | 9/1994 | Lee | 364/709 |
| 5,363,227 A | 11/1994 | Ichikawa et al. | 359/83 |
| 5,363,276 A | 11/1994 | Crockett | 361/752 |
| 5,375,076 A | 12/1994 | Goodrich et al. | 364/708.1 |
| 5,383,138 A | 1/1995 | Motoyama | 364/708.1 |
| 5,410,333 A | 4/1995 | Conway | 345/169 |
| 5,410,447 A | 4/1995 | Miyagawa | 361/681 |
| 5,416,730 A | 5/1995 | Lookofsky | 364/708.1 |
| 5,481,430 A * | 1/1996 | Miyagawa et al. | 361/681 |
| 5,494,447 A | 2/1996 | Zaidan | 439/31 |
| 5,574,481 A | 11/1996 | Lee | 345/168 |
| 5,666,694 A * | 9/1997 | Slow et al. | 361/681 |
| 6,256,017 B1 * | 7/2001 | Bullister | 345/168 |

* cited by examiner

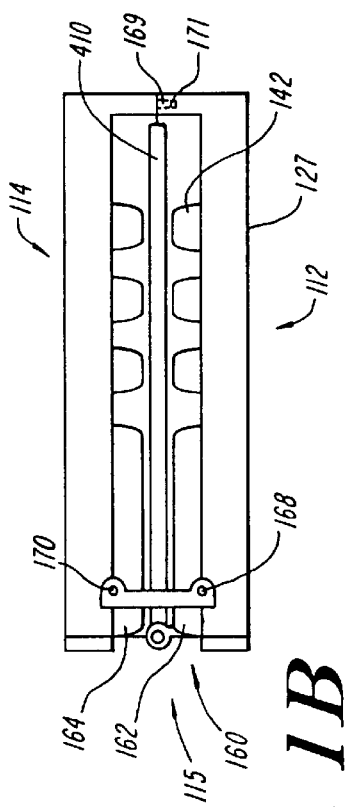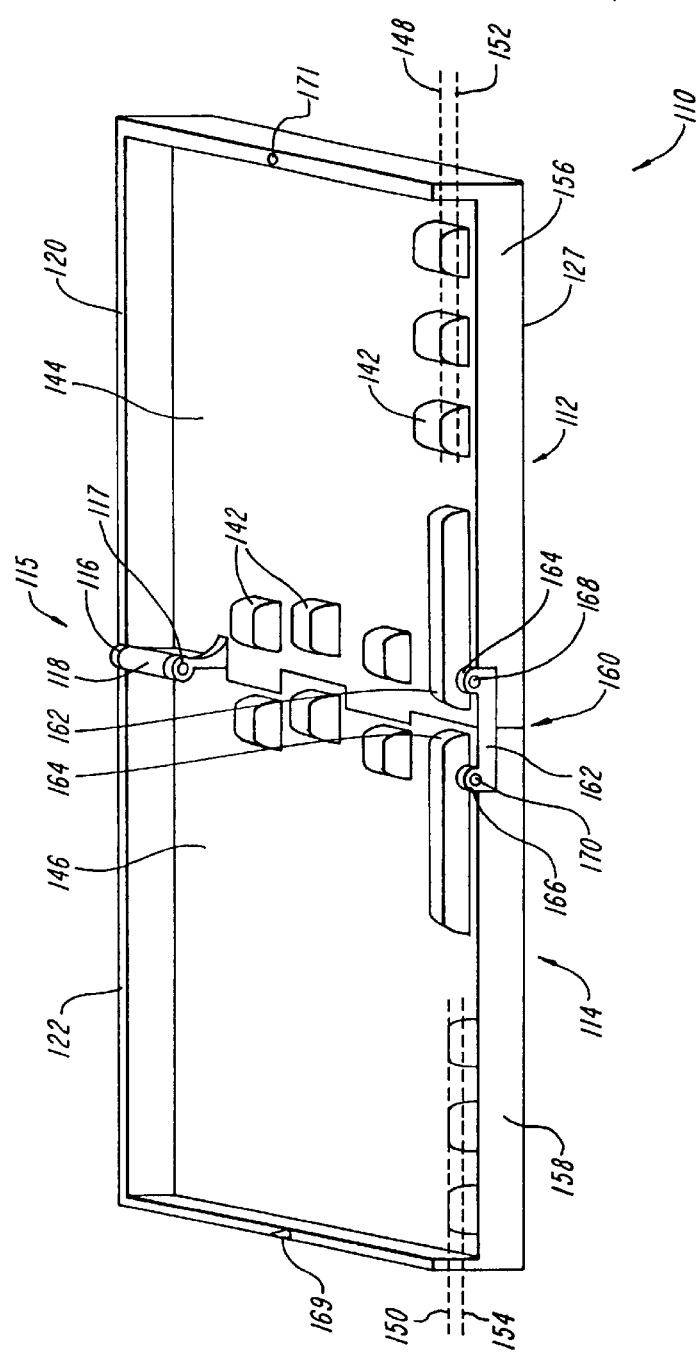

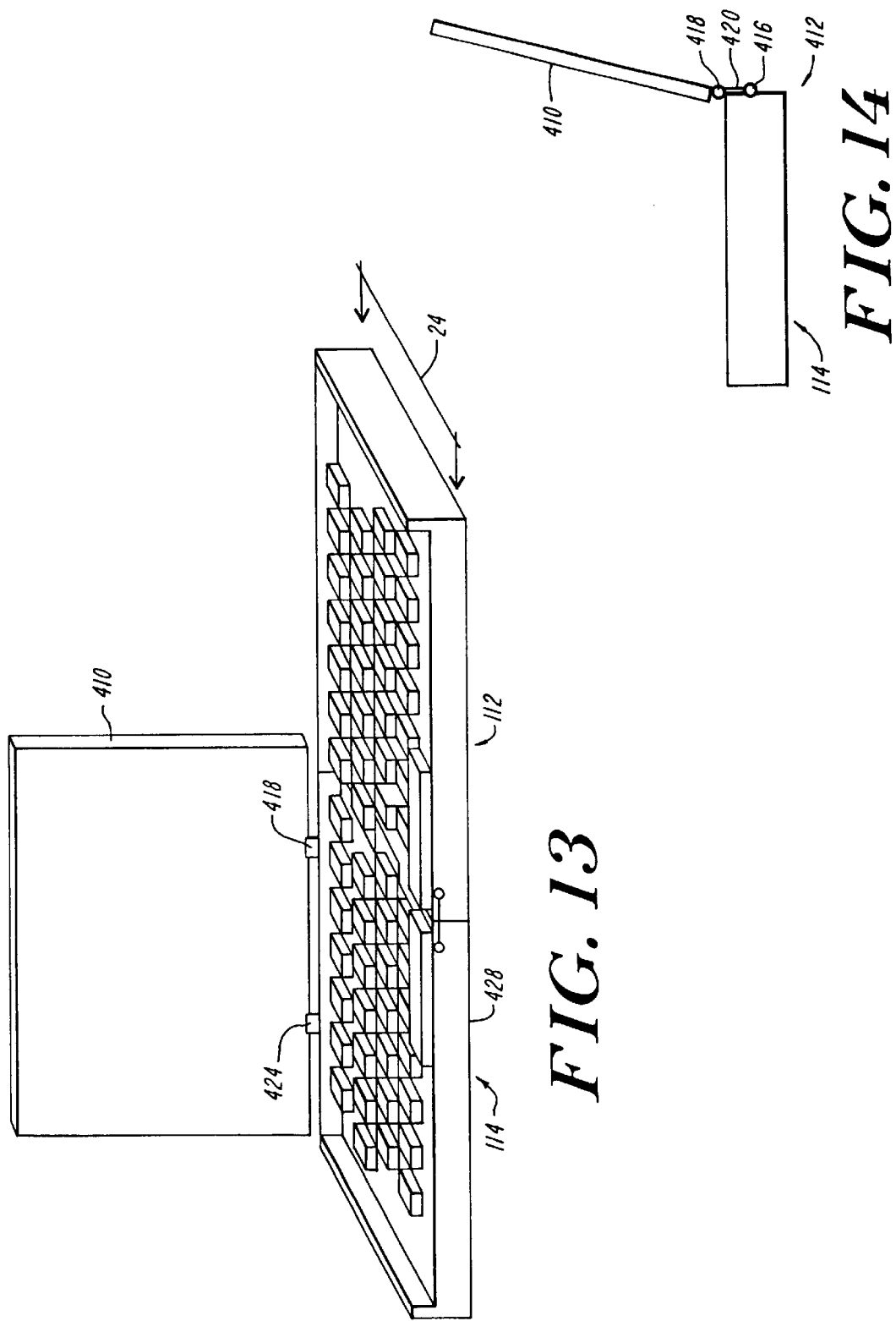

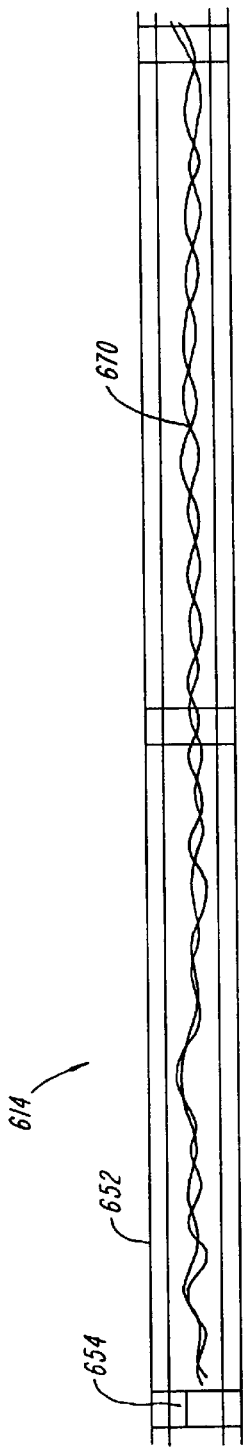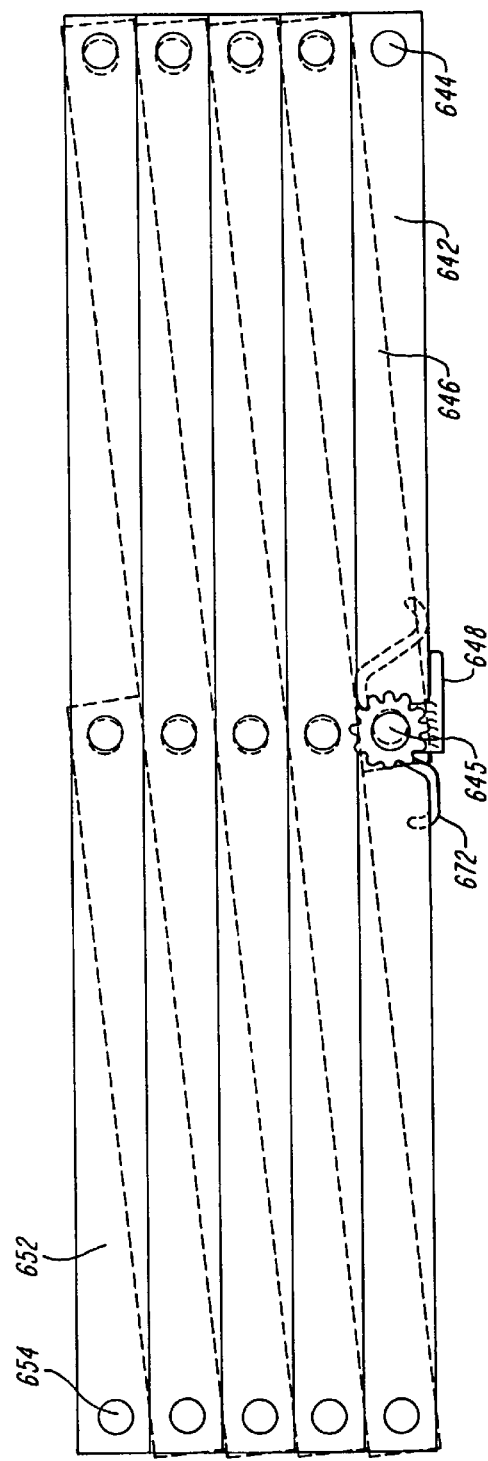

MULTIFUNCTIONAL PORTABLE COMPUTING DEVICE WITH SPECIAL HOUSING

This application is a divisional application which claims priority on co-pending Ser. No. 09/122,677, filed Jul. 27, 1998, now U.S. Pat. No. 5,996,796 which was a division of Ser. No. 08/558,688, filed Nov. 16, 1995, now abandoned to which priority is also claimed.

BACKGROUND—FIELD OF INVENTION

The invention relates to portable computers and specifically to portable computers with housings that can be reconfigured to perform multiple tasks.

BACKGROUND—PRIOR ART

The miniaturization of electronic devices, and particularly portable devices, has generated the need for a keyboard which can collapse to the compact size of the portable device. The keyboard must also expand from the compact state to an extended state which is large enough to accommodate the fingers of human hands. A mechanism is needed to provide for a smooth and reliable collapse and extension of the keyboard. The mechanism should also maintain alignment of the components and should not interfere with the typing.

The miniaturization of electronic devices, and in particular their evolution into portable devices, has generated the need for method to protect and store the display during transport. The display should be movable to several positions so that a display of compact size can give a wide range of functionality to the portable device.

In collapsible computing devices, the display typically pivots from a closed position to an adjustable open position. Each time the device is opened, the user needs to manually readjust the display to the desired viewing angle. Other pivoting components may need a similarly reproducible adjustment. The requirement to read-just each pivot each time the device is opened compromises the convenience of the device and limits the number of pivoting components that can be used in a practical device. Thus, there is a need for a pivoting mechanism that can reproduce a desired angle without the need for manual adjustment.

Portable computing devices are generally supported on table surfaces which are significantly below the eye level of the user. The display size of such devices is limited by a desire for compactness. There is a need for a mechanism to raise the display of these portable computing device closer to the eyes of the user to provide greater readability.

Each of the various portable computing devices available can meet specific needs. Laptop computers provide the full functionality of a keyboard, pointing device, and large display screen. However, they are generally very bulky and heavy. Very compact handheld computing devices lack the functionality of a laptop computers.

To get the full range of uses of a computing device, a user must use several devices. This requires redundant investment in the hardware, software, and training. It also requires additional maintenance of the hardware, software, and battery charge.

Thus, there is a need for a design which can combine many functionalities into a single device.

OBJECTS AND ADVANTAGES

It is an object of the invention to provide:

a) an ergonomic keyboard with a hinging mechanism which does not interfere with typing, yet lets the keyboard collapse into a more compact form;

b) a keyboard hinging mechanism which is simple, reliable, and inexpensive;

c) a keyboard hinging mechanism which maintains alignment of the keyboard sections during the collapse of the keyboard, and rigidly connects the keyboard sections in the fully collapsed condition;

d) a keyboard hinging arrangement which facilitates the routing of wires between the keyboard sections;

e) a keyboard hinging mechanism which allows the keyboard sections to open to a split configuration, with a greater spacing at the front for more natural positioning of the hands.

It is a further object of the invention to:

a) allow a display to share the footprint of a folded keyboard;

b) allow the display to move to and from a protected position for transport;

c) allow the display to move to an adjustable, inclined position leaving a keyboard accessible for typing;

d) allow the display to move to flat position alongside the housing for pen input;

e) allow the display to move to an inclined position in which the device is suitably stable for pen input;

f) allow the display to be positioned in the front of the device so that the housing can be hidden from view;

g) provide cushioning to protect the display;

h) eliminate the need to readjust the display angle each time the computer is opened;

i) minimize the force required to move the display between the open and closed positions;

j) reduce the difficulty and number of steps required to open and close the computer;

k) provide a device which can open using only pivoting movements;

l) provide a stable configuration of the device in which the display is extended toward the user for enhanced readability.

It is a further object of the invention to provide a combined multifunctional portable computing device for which:

a) the user need invest in only a single device, so that the expense of redundant electronic devices is avoided;

b) a charge need be maintained only on a single set of batteries;

c) the bulk of carrying several devices is avoided;

d) the expense of buying several sets of software is avoided;

e) the labor in installing multiple sets of software and maintaining several operating systems is avoided;

f) the expense and labor in translation between incompatible sets of software is avoided;

g) the training for several different devices and input paradigms is avoided.

SUMMARY

Keyboard

According to the invention, the keyboard is divided into two sections. In the open, extended position the sections are arranged side by side so that a standard arrangement of keys such as the "QWERTY" arrangement can be accomodated.

In one embodiment the keyboard sections abut directly against one another in the open position such that the keytop surface is continuous.

In another embodiment, the front portion of the keyboard sections are separated in the open position. This spacing orients the keyboard sections at an outward angle. This angle reduces the flexing of the wrists and gives a more natural and comfortable typing position.

One of the keyboard sections is pivotally supported to swing about an axis located above the plane forming the keytop surface. To collapse, this section swings 180 degrees so that the keytop surfaces are in face-to-face relationship. A display may be stored between these keytop surfaces in this collapsed condition. This display may have a size and aspect ratio similar to that of each of the keyboard sections.

In some embodiments of the invention, a combination of two different types of pivotal connections connect the two keyboard sections. Connected to the rear portions of the keyboard sections are two lugs which extend above the keytop surfaces and are connected by a single axle. This axle defines a single axis of rotation. This axle may be hollow to facilitate the routing of wires. In contrast, the front portions of the keyboard sections are connected through a link which retracts below the keytop surface in the open position. At each end of the link a lug connects the link through an axle to a corresponding lug attached to each keyboard section. An alignment pin secures the keyboard sections in the closed position.

Display

The display hinging mechanism enables the display to move between several positions. It enables a single portable device to perform several functions.

A double-acting hinge connects the display to a keyboard base. The first part of the hinge pivots the display from a storage position face-down on the top of one keyboard section to a typing position at an angle inclined above the keyboard. The second part of the double acting hinge allows the display to pivot further around to lay on the reverse surface of the keyboard section. In this position the display is accessible for pen input.

A prop can position the display at an angle above the reverse surface of the keyboard section. The prop completes the third segment of a triangular configuration formed with the display and the keyboard section.

In this propped configuration, the heavy components incorporated into the keyboard housing form a stable base. The display faces outward and upward from the triangular configuration, so that is fully visible and hides the prop and base from view. Forces applied onto the display by pen input are directed to a point on the base, so that the device is very stable against tipping when forces from pen are applied to a propped display.

This transition of the display from the storage position to the laptop position to the propped position to the flat pen input position is effected only through hinging motion about two axes of a simple double-acting hinge. This movement is easily effected and does not require any complex translations or combinations of sliding and rotating motions.

An adjustable stop can be used in conjunction with the pivots to reproduce a previous pivot angle without the need for manual adjustment.

Link Mechanisms

A portable computing device uses a pair of link mechanisms to raise its display toward the user for better readability. The link mechanisms can collapse from an open, extended configuration to be stored within the collapsed computing device. The heavy components of the device are incorporated into the keyboard components so that the center of gravity of the device is very low. This provides a stable base from which the display can be supported. A set of adjustable stops enable the display to be reproducibly raised to the desired viewing position. The closer viewing position allows a smaller, pocket-sized display to fulfill the function of a larger laptop display with a smaller area and correspondingly lower power consumption.

BRIEF DESCRIPTION OF THE DRAWING

FIG. 1A shows a first embodiment of the keyboard in an open, extended position.

FIG. 1B shows the first embodiment of the keyboard in the collapsed condition.

FIG. 13 shows the device fully opened to a position suitable for keyboard input.

FIG. 14 shows an end view of the configuration of FIG. 13.

FIG. 25 is a top view of a vertically stacked link mechanism.

FIG. 26 is a side view of a vertically stacked link mechanism.

DESCRIPTION OF THE SPLIT KEYBOARD SHOWN IN FIGS. 1–3

Figure 2:
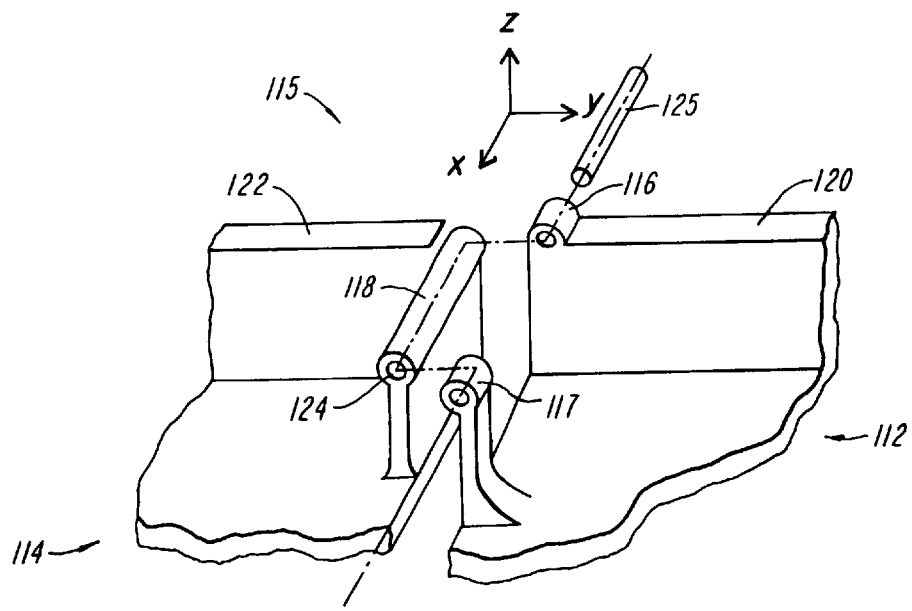
FIG. 2 is an exploded view of the first pivot mechanism in the first embodiment.

FIG. 1A shows a keyboard 110 split into two keyboard sections, a right keyboard section 112 and a left keyboard section 114. These keyboard sections fold to the collapsed condition shown in FIG. 1B.

A split keyboard and display was disclosed in the co-pending commonly owned U.S. patent application Ser. No. 08/515,383, filed Aug. 15, 1995, which was a continuation of U.S. patent application Ser. No. 08/202,333, filed Feb. 24, 1994. The title was "A Collapsible Keyboard and Display Mechanism for a Computer System". These parents of the present application are expressly incorporated in full here by reference.

The xyz coordinate system is fixed with respect to keyboard section 112. The x-y plane is parallel to a bottom surface 127 of keyboard section 112. The x-axis coincides with the rotation axis of the first pivot mechanism 115. X is zero at the rear end of the first pivot mechanism 115.

A first pivot mechanism 115 is detailed in the exploded view of FIG. 2. Lugs 116 and 117 and are attached to keyboard section 112 proximate to its rear portion 120. Lug 118 is attached to keyboard section 114 proximate to its rear portion 122. A journal bearings 124 lines lug 118. An axle 125 connects the lugs. Thus, the lugs and journal bearings act as axle bearing members. The first pivot mechanism restricts the pivoting of keyboard section 114 with respect to section 112 to rotations about the x-axis shown in FIG. 2.

Figure 3:
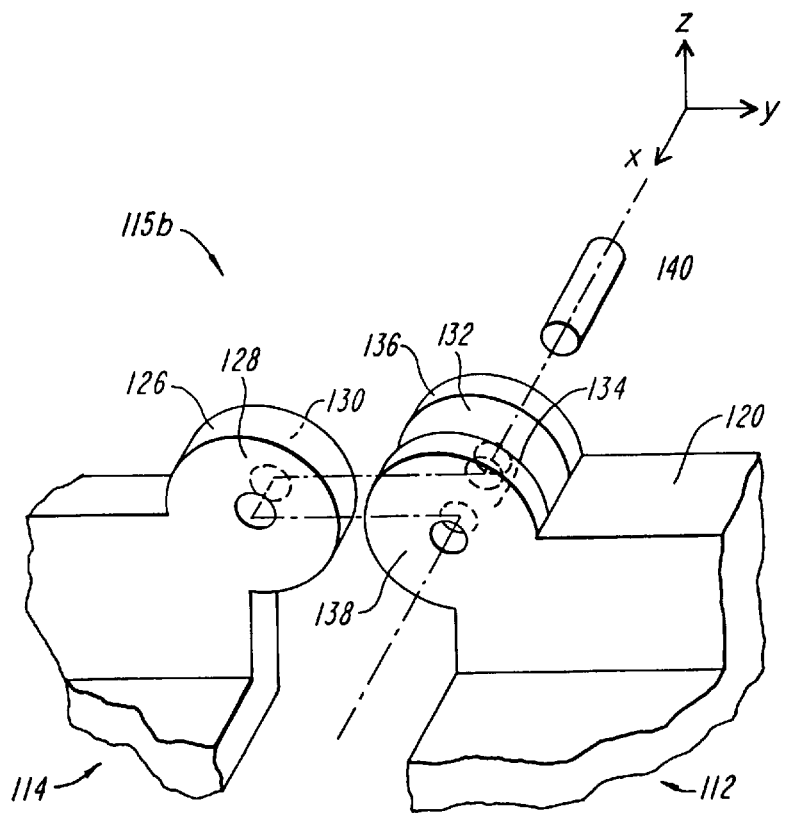
FIG. 3 is an exploded view of an alternate first pivot mechanism in the first embodiment.

An alternate configuration 115b of a first pivot mechanism is shown in the exploded view of FIG. 3. Lug 126 has thrust bearing surfaces 128 and 130. These surfaces mate with thrust bearing surfaces 132 and 134 of lugs 136 and 138, respectively. An axle 140 pivotally connects the lugs. This alternate first pivot mechanism restricts the pivoting of keyboard sections 114 with respect to section 112 to rotations about the x-axis shown in FIG. 3.

Both pivot mechanisms 115 and 115b align the rotation of the keyboard components about the x-axis and resist rotations about the y- and z-axes. Pivot mechanism 115 incorporates a journal bearing 124 of an extended length to provide a moment arm against torques in the y- and z-axes. Pivot mechanism 115b incorporates thrust bearings 126, 128, 132, and 134 of an extended diameter to provide a moment arm against torques in the y- and z-axes.

As shown in FIG. 1A, plurality of touch responsive keys 142 protrude from top surfaces 144 and 146 of respective keyboard sections 112 and 114. The tops of (undepressed) keys 142 define keytop surfaces 148 and 150, which are approximately planar and parallel to respective top surfaces 144 and 146. Keys 142 are movable to a depressed position. Depressed keytop surfaces 152 and 154 correspond to the plane defined by the tops of keys 142 in a depressed position. Depressed keytop surfaces 152 and 154 lie approximately 3mm below keytop surfaces 148 and 150, respectively.

The rotation axes of first pivot mechanisms 115 and 115b can be located on keytop surfaces 148 and 150. For embodiments in which a display is stored in a space between keyboard sections 112 and 114 in the collapsed condition, the rotation axes of pivot mechanisms 115 and 115b are located above the keytop surfaces 148 and 150.

A second pivot mechanism 160 connects the keyboard sections 112 and 114 proximate to their respective front portions 156 and 158. This pivot mechanism 160 may be hidden from view behind the space bar. A link 162 is pivotally attached to lugs 164 and 166 through axles 168 and 170. In the open condition, the link 160 retracts beneath the keytop surfaces 148 and 150.

When the keyboard 110 is in the open position, the top inner surfaces 162 and 164 of the subset of keys 142 which are adjacent to the abutting surfaces are spaced from one another. This spacing prevents interference between the surfaces 162 and 164 during the pivoting about axles 168, 170, and 125 while collapsing the keyboard. During collapse, the front portion pivots through an arc whose radius is one-half the distance between the centers of axles 168 and 170. In some configurations, the subset of keys 142 adjacent to the abutting surface may depress one another during the collapse to achieve clearance.

In the collapsed condition of FIG. 1B an alignment pin 169 in keyboard section 114 mates with a cavity 171 in keyboard section 112. Alignment pin 169 in combination with first pivot mechanism 115 secure keyboard sections 112 and 114 against relative sliding in the x-y plane. Furthermore, alignment pin 169 is spaced a distance from the first pivot mechanism 115 to provide a moment arm to resist torques about the z-axis and prevent relative rotations about the z-axis.

In the collapsed condition of FIG. 1B, a display may be protected between the keyboard sections 112 and 114. When keyboard sections 112 and 114 are exposed to shock or bending, the display may remain cushioned and isolated from the shock and in a planar condition by the keys 142 being selectively depressed by the display. The display is free to move in the region between the depressed keytop surfaces 152 and 154.

The spacing of the keyboard components 112 and 114 is maintained in the collapsed condition by pivot mechanisms 115 and 160 and by pin 169. Thus, the spacing ot the planar keyboard sections is maintained at three points. Furthermore, these three points are distributed at distant ends of the planar keyboard, so that each portion of the keyboard sections is well supported. This rigid structure is capable of protecting a display stored between the collapsed keyboard sections 112 and 114.

This configuration results in a keyboard which can collapse to a rigid structure, which has a pivot mechanism 115 in the rear which can maintain a well-defined pivot axis during collapse, and which has a pivot mechanism 160 in the front portion which retracts so as not to interfere with typing.

This combination of features was achieved using pivots in which only rotational movement is required. These rotational pivots have several advantages over sliding members. The rotational pivots are simple and sturdy. Their bearings are easily sealed to retain lubrication and to prevent debris from entering and interfering with their operation. The sliding motion within pivoting components is proportional to the axle diameter, and their total sliding distance is usually less than than the translational motion of sliding members. This results in less frictional energy consumed for easier and smoother movements. Their axle diameter can be reduced to further reduce the frictional torque and to give smoother operation. The combination of the axle's cylindrical journal bearing surfaces and circular thrust bearing surfaces restrict the motion to a single rotational degree of freedom and are very stiff against other movements. Wires may be routed through a hollow axle for protection and to guide them through a well-defined torsional flexure.

DESCRIPTION OF THE KEYBOARD AND SHROUD SHOWN IN FIGS. 4–8

Figure 4:
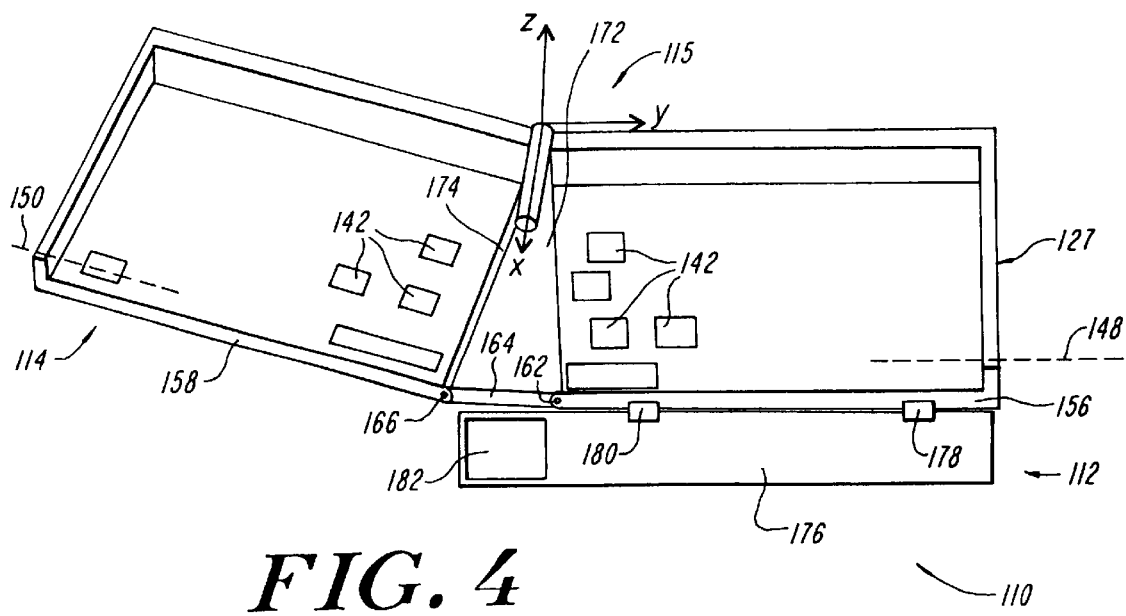
FIG. 4 shows a second embodiment of the keyboard in an open position in which the front of the keyboard sections are spaced from each other.

FIG. 4 shows an alternate embodiment of the keyboard 110 in the open position. The front portion of the inward facing surfaces 172 and 174 are spaced from each other. As a result, the keyboard sections 112 and 114 are oriented at a relative angle. This "natural" position may reduce the required flexure of the user's wrists and provide him with a more comfortable typing position.

In this embodiment the inward facing surfaces 172 and 174 do not abut against one another and may be smooth surfaces. In the closed position shown in FIG. 5, the lugs 164 and 166 may protrude from keyboard sections 112 and 114.

Figure 5:
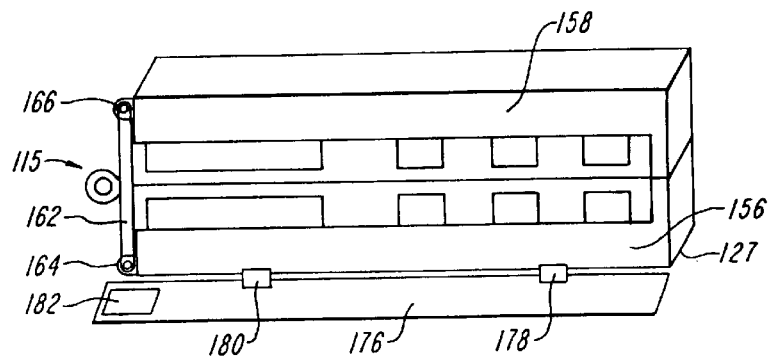
FIG. 5 shows the second embodiment of the keyboard in a collapsed condition.

When the keyboard 110 is in the open position, its front portions 156 and 158 lie below the keytop surfaces 148 and 150 to allow the user's hands to access the keys 142. As shown in FIG. 5, this results in a gap between front portions 156 and 158 in the closed position.

Figure 6:
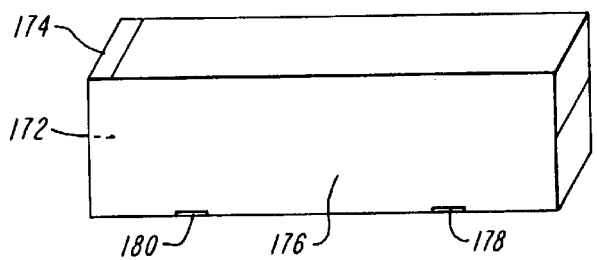
FIG. 6 shows a shroud covering the front portion of the second embodiment of the keyboard in the collapsed condition.

To cover this gap, a shroud 176 is attached through pivot mechanisms 178 and 180 to the bottom of front portion 156. The shroud 176 is shown in FIGS. 4 and 5; first in an extended position in which its bottom surface is coplanar with the bottom surface 127 of the keyboard section 112. The shroud 176 can pivot to a second position shown in FIG. 6 in which it covers the front portions 156 and 158 as well as the intervening gap. The shroud 176 is positioned in the keyboard front, so that a display which may be connected to the rear of the keyboard can pivot to a pen input position without the need to move the shroud 176.

A touch-sensitive surface 182 is attached to the shroud 176. When the shroud is in the second position (see FIG. 6), this surface is protected from damage. When the shroud 176 is in the first, extended position, the touch sensitive surface 182 is accessible to the user's thumbs. This touch sensitive surface supplements the keyboard input with tracking and pointing information.

Figure 7:
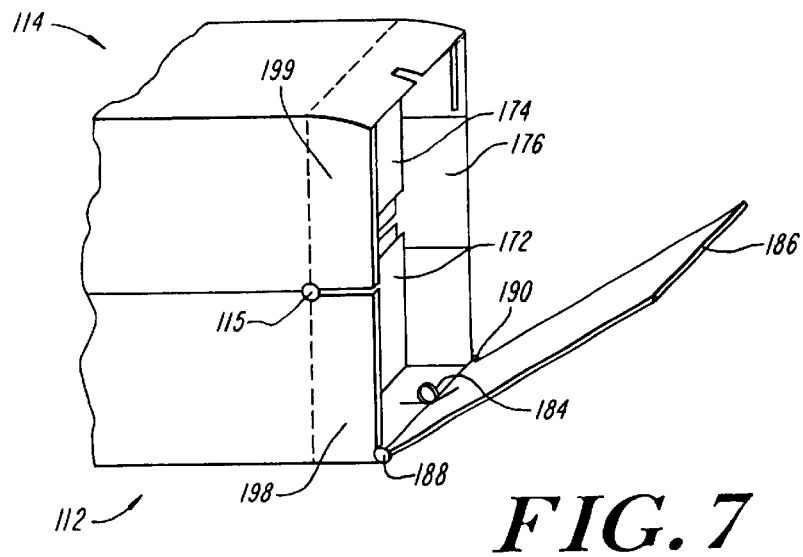
FIG. 7 shows a shroud pivoting to cover the end portions of the second embodiment of the keyboard in the collapsed condition.

FIG. 7 shows a rear view of the keyboard 110 in the collapsed condition. Upon collapse of the keyboard 110, a spring 184 rotates a second shroud 186 about a pair of coaxial pivots 188 and 190 to cover the surfaces 172 and 174.

Figure 8:
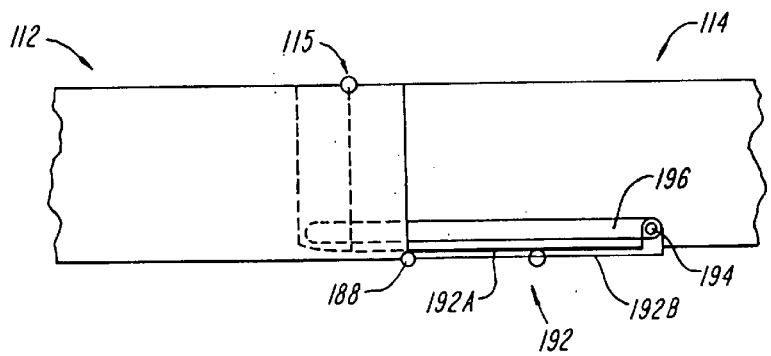
FIG. 8 shows a shroud when the keyboard is in the extended position.

FIG. 8 shows a rear view of the keyboard 110 on the open position. A shroud 192 is similar to shroud 186 in dimensions and configuration in the opened and closed positions. The shroud 192 differs in that it employs a grooved engagement system rather than a spring closure mechanism. A section 192a of shroud 192 is attached to keyboard section 112 through pivots 188 and 190. A section 192b of shroud 192 is pivotally attached to section 192a and is slidably engaged to keyboard section 114 through pin 194 and groove 196.

Overhanging surfaces 198 and 199 of keyboard sections 112 and 114, respectively, mate with shroud 186 in the closed position. In the open position, surface 198 and 199 are adjacent.

In the embodiments of FIGS. 7 and 8, the locations of shrouds 186 and 192 are constrained only by the furthest protrusion of irregular surfaces 172 and 174.

This distance is one-half a key width beyond the axis of the keyboard pivot 115. This distance need not be as large as the thickness of keyboard sections 112 and 114. This results in a collapsed keyboard of reduced length.

DESCRIPTION OF THE KEYBOARD AND DISPLAY IN FIGS. 9—20

Figure 9:
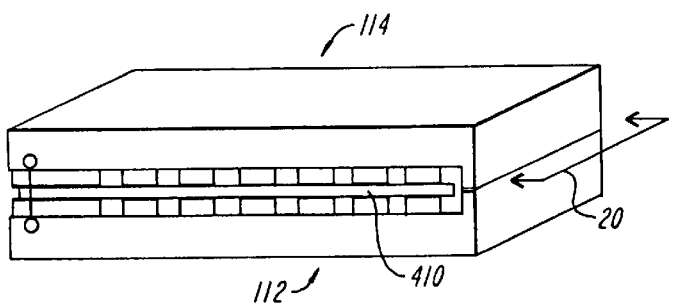
FIG. 9 shows the display in the protected position between the folded keyboard sections.
Figure 10:
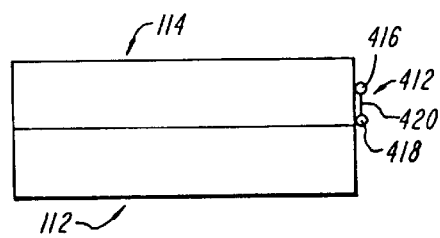
FIG. 10 shows an end view of the configuration of FIG. 9.

FIGS. 9 and 10 show the display 410 in the protected position. The keyboard sections 112 and 114 protect the display 410. The display 410 is movable between keyboard sections 112 and 114 to isolate the display 410 from shock, impact, and bending of keyboard sections 112 and 114.

Double acting hinges 412 and 414 allow the display 410 to pivot with respect to keyboard component 114. Hinge 412 has two axle pivot members. Pivot 416 is attached to the keyboard section 114. Pivot 418 is attached to the display 410. Link 420 connects pivot 416 and 418. Similarly, hinge 414 has two axle pivot members. Pivot 422 is attached to the keyboard section 114. Pivot 424 is attached to the display 114. Link 426 connects pivot 422 and 424. sections Further protection against shock may be provided by extendable links 420 and 426. Extension and compression of these links allows the portion of the display adjacent to the hinges 412 and 414 to translate toward and away from the keyboard section 112. Alternately, an elastomeric connection between the display 410 and the pivots 418 and 424 may provide this cushioning effect.

Figure 12:
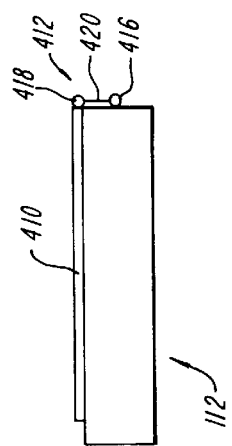
FIG. 12 shows an end view of the configuration of FIG. 11.
Figure 11:
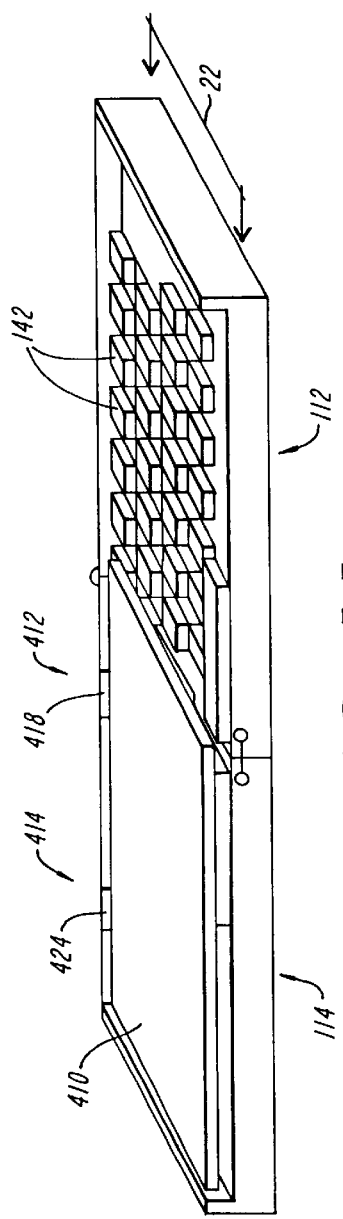
FIG. 11 shows the device in a partially open position in which the keyboard is in the extended position.

Pivoting keyboard section 114 through an angle of 180 degrees to the extended position results in the configuration shown in FIGS. 11 and 12. Throughout this first pivoting movement the display 410 remains in a fixed, face-down position with respect to keyboard section 114.

In a second pivoting movement, the display is raised to the configuration shown in FIGS. 13 and 14 by pivoting pivots 418 and 424. The display angle may be adjusted by adjusting the pivoting angle of pivots 418 and 424.

Figure 16:
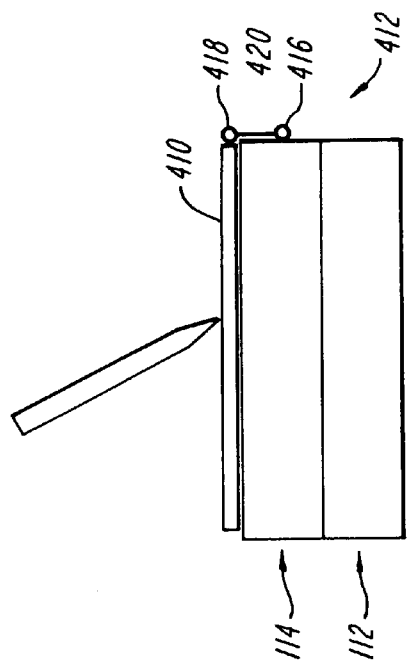
FIG. 16 shows an end view of the configuration of FIG. 15.
Figure 15:
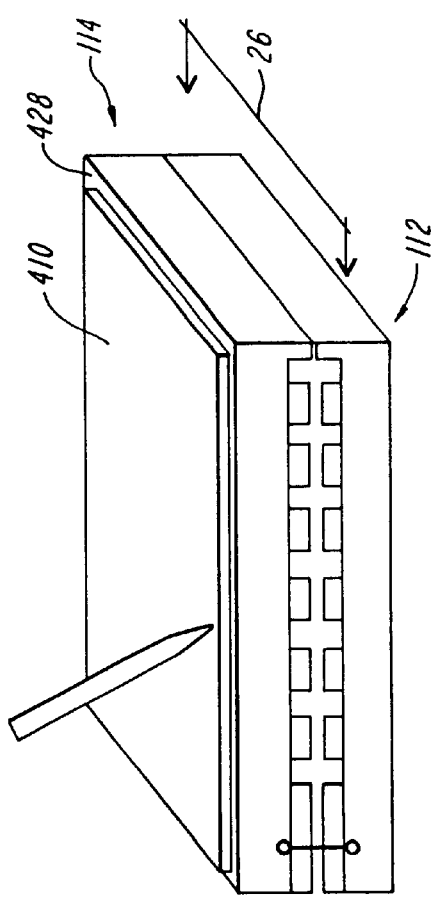
FIG. 15 shows the display in a position on top of the folded keyboard, with the display surface exposed for pen input.

The double-acting hinges 412 and 414 allow the display 410 to further pivot with respect to the keyboard section 114. First, the display further pivots about pivot 418 and 424, so that it extends horizontally outward, 180 degrees from its position in FIGS. 11 and 12. Next, the second pair of pivots 416 and 422 rotate an additional 180 degrees so that the display lies against the reverse surface 428 (opposite from the keys) of keyboard section 114. The double-acting hinge allows this to be accomplished in a single rotating movement, which simplifies the process of changing the device configuration. Finally, the keyboard sections are folded so that the device is configured as in FIGS. 15 and 16.

Figure 17:
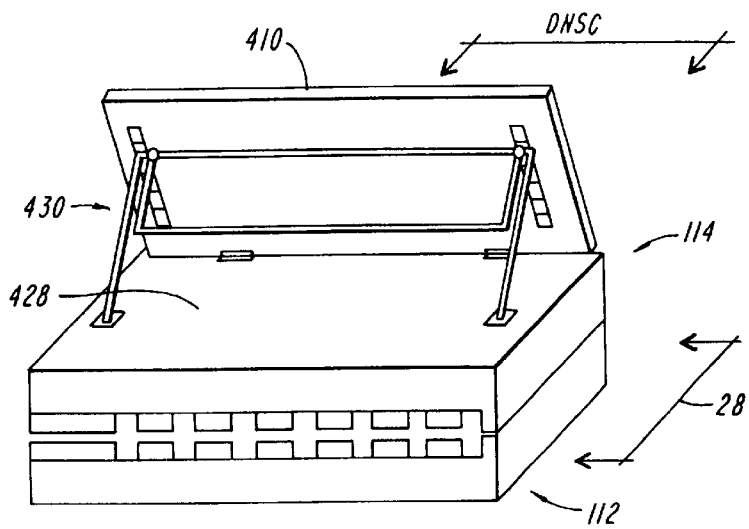
FIG. 17 shows the device with the display in a propped position on top of the folded keyboard.
Figure 18:
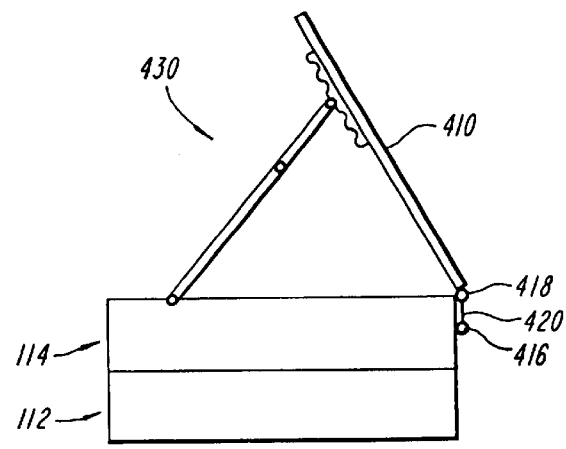
FIG. 18 shows an end view of the configuration of FIG. 17.
Figure 19:
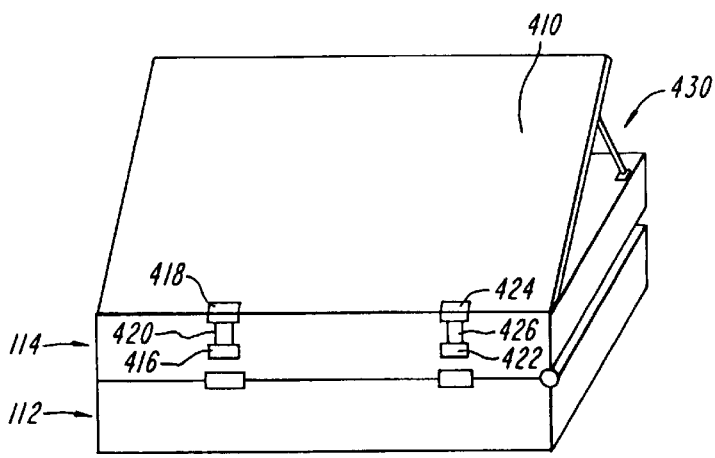
FIG. 19 shows a front view of the configuration of FIG. 17.

FIGS. 17, 18, and 19 show a propped configuration. Prop 430 is pivotally connected to keyboard section 114. The display 410 rests against the prop 430. The propped angle of the display 410 may be adjusted by adjusting the location at which the prop 430 supports the display 410.

FIGS. 17, 18, and 19 show a very compact and stable triangular configuration of the device. Only simple pivoting joints are needed, and they are not required to bear the large torques that would be needed to resist rotation of a cantilevered prop. Typically a cantilevered prop must be rotatable to various angles with respect to the device housing, and a mechanism is needed to adjust the angle and to maintain the desired angle against torques arising from forces applied at the end of the arm.

There are several advantages to this configuration. The first is stability. The heavy components, including the batteries and electronics, are located in a base formed by keyboard sections 112 and 114. This base lies flat on the table. Only the bare display 410 need be elevated. This results in a stable configuration with very low center of gravity. The display 410 is located directly above this heavy stabilizing base. Furthermore, the forces imparted by a pen push both downward and backward on the tilted display 410. Because the display is located above the front portion of the base, these forces are directed toward the base, so that the device is further stabilized against tipping. In contrast, the forces applied to the display located in the rear of a standard notebook computer tend to tip it over backwards.

The second advantage to this configuration is accessibility. The display 410 surface faces outward so that no other components block access for pen input. The display 410 is located close to the table surface on which the device rests. The display 410 can be accessible for pen input by a hand resting on the table surface. This configuration also results in a very small footprint, so that it may sit unobtrusively on a desk, much as a clock or calendar may sit. In this configuration with a calendar program running, it may in fact function as a calendar, appointment book, and alarm clock. This configuration also results in a very small visual "footprint"; normally only the visual area of the display 410 is seen by the user. This display 410 largely blocks from view the other computer components and leaves the user's field of view uncluttered.

The third advantage is simplicity. The main components, the display 410 and the keyboard sections 112 and 114, are connected through a set of simple pivots. Only rotational movement of the pivots is needed; no sliding motion required. The prop 430 can be attached to the keyboard component, so that the prop 430 need add the weight and volume to the display 410.

The triangular configuration is very stable structurally. Each of the triangle's three contact points needs to support forces but does not need to support torques. The need for the very strong clutches or splines to support a cantilevered prop is obviated.

Figure 20:
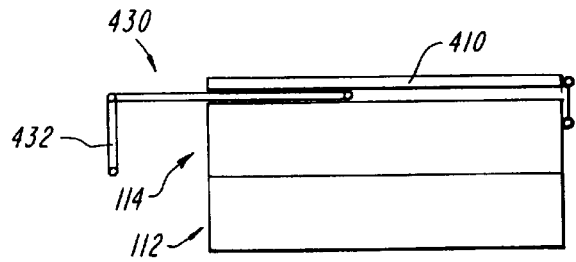
FIG. 20 shows an end view of the device in a transport configuration. The prop protrudes outward from the device to function as a handle.
Figure 21:
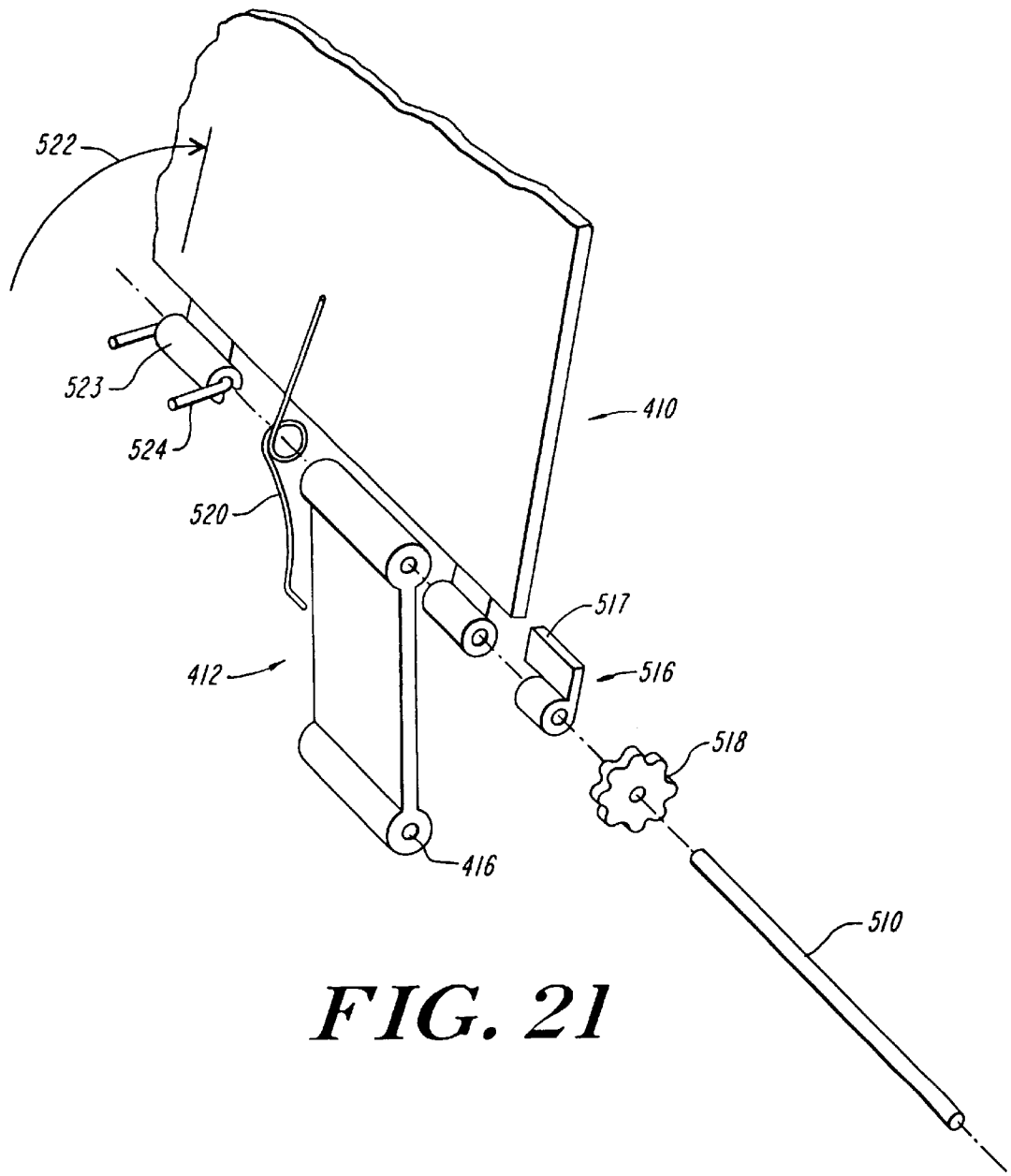
FIG. 21 details a pivot mechanism with a spring-loaded stop and a releasable catch for a double-acting display hinge.

A configuration suitable for transport is shown in FIG. 20. The prop 430 can be moved to a position in which is protruded outward from the keyboard section 114. A handle 432 pivots out from the prop 430 to a position centered between keyboard sections 112 and 114. In this position, the device will hang vertically below the centered handle 432 with the center of gravity of the assemble of keyboard sections 112 and 114 directly beneath the handle 432.

Thus, this single, simple, compact device can assume several positions. It can fold to enclose and protect the display. It can open to a typing configuration similar to a laptop. Its keyboard can fold with the display lying flat to accept pen input. It can open to a triangular configuration for a desktop display and pen input device.

DESCRIPTION OF THE ADJUSTABLE STOP OF FIG. 21

A shaft 510 connects a first pivoting component to a second pivoting component. In FIG. 20, these pivoting components are the double-acting hinge 412 and the display 410. The shaft 510 is rigidly attached to the hinge 412. The display 410 is free to rotate about the shaft 510. An adjustable stop 516 frictionally engages the shaft 510. An arm 517 protrudes from the adjustable stop. A knob 518 is rigidly attached to the stop 516 and accessible for manually adjusting the angle of the stop 516 with respect to the shaft 510.

A spring 520 is wrapped around the shaft 510 and engages the hinge 412 and the display 410. The display 410 is held between the spring 520 and the arm 517 at a specified viewing angle 522 with respect to a horizontal. This viewing angle 522 can be increased by rotating the stop 516 in a clockwise direction. This clockwise rotation of stop 516 can be effected by rotating either the knob 518 or the display 410 in a clockwise direction. The viewing angle 522 can be decreased by rotating the knob 518 in a counter-clockwise direction. Thus, adjustment of the angle of the stop 516 relative to the shaft 510 corresponds to an adjustable and reproducible display angle 522.

This adjustment allows display 410 to freely pivot through angles less than or equal to the display angle 522. The torque imparted by the spring 520 to the display 410 may be slightly larger than the torque imparted by gravity. This gravitational torque can be calculated as the weight of display 410, times the distance of the center of gravity of the display 410 to its axis of rotation, times the cosine of its angle with respect to the horizontal. Through this counter-balancing of torques, the spring-loaded display 410 can easily and automatically close and open reproducibly to an angle 522 predetermined by the most recent adjustment of stop 516. Manual adjustment is needed only when this predetermined angle 522 is to be changed. This adjustable stop 516 obviates the need for routine adjustment each time the display is opened. This makes the compact computing device more convenient to use.

Adjacent to the double-acting hinge 412 is a mechanism which restricts the movement of the double-acting hinge. A "C"-shaped catch 523 is attached to the display 410. A "U"-shaped bar 524 is attached to a horizontal keyboard section (not shown). When angle 522 is less than 180 degrees, the catch 523 is constrained to rotate around the bar 524. This occurs when the display 410 is to be used in the typing configuration shown in FIGS. 13 and 14.

When the angle 522 is increased to 180 degrees, the catch 523 is released from the bar 524, allowing the display 410 to pivot an additional 180 degrees about pivot 416. This enables the display 410 to pivot to the reverse surface 428 of the keyboard section 114. This position (shown in FIGS. 15 and 16) allows pen input.

In this way, the double-acting hinge 420 acts as a single hinge in the typing position, where the display angle 522 is less than 180 degrees. The stop 516 can be used to maintain a preset display angle 522 suitable for typing. When the display angle 522 is increased to 180 degrees, the catch 523 releases to allow the double-acting hinge 412 to swing around in a single, natural movement to the pen input position shown in FIGS. 15 and 16.

DESCRIPTION OF THE LINK MECHANISMS OF FIGS. 22–27

Figure 22:
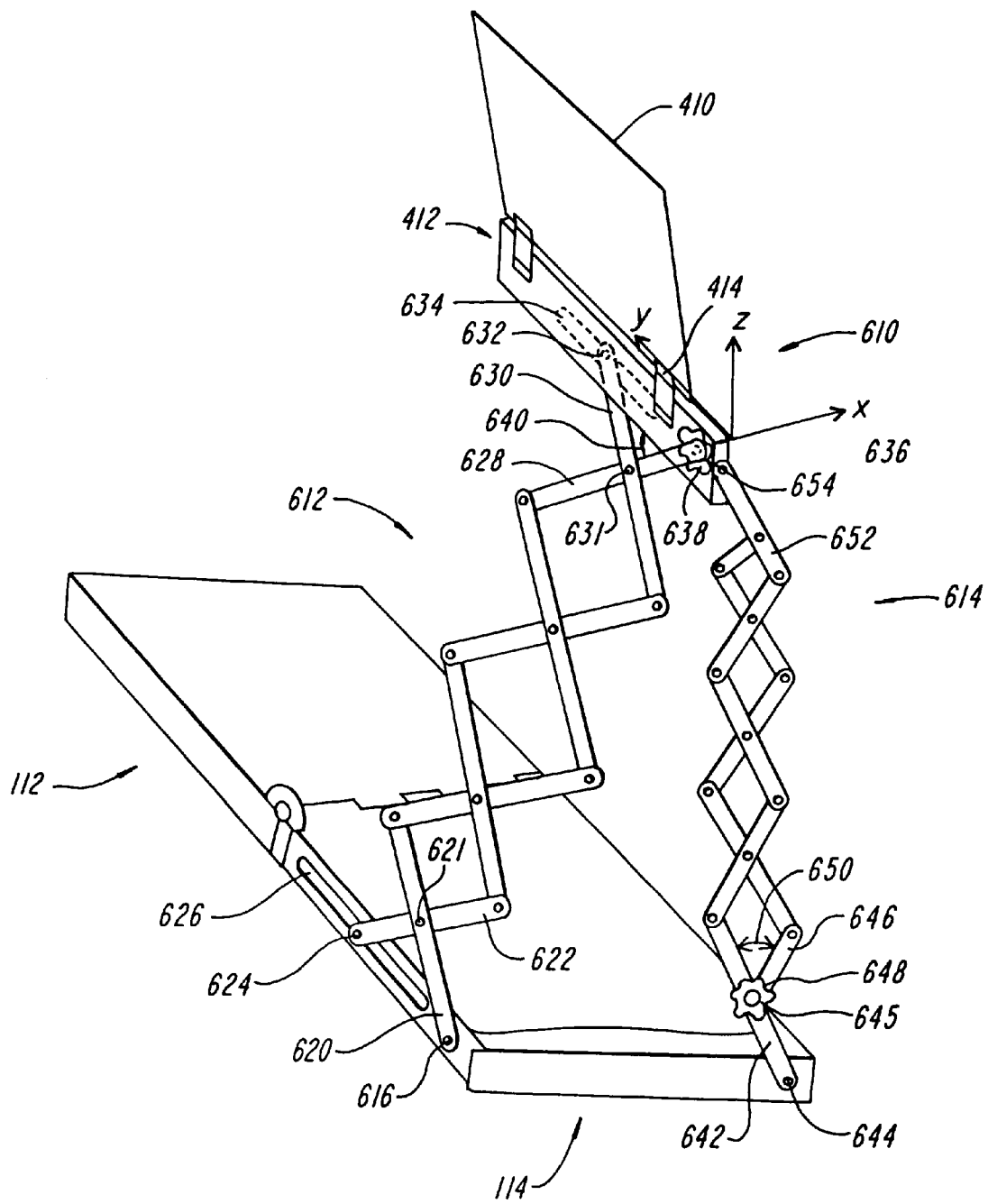
FIG. 22 shows a display of a compact computing device supported by two link mechanisms.

In FIG. 22, a pair of keyboard sections 112 and 114 form a base for supporting a display 410. The more massive components of the portable computing device such as the batteries, disk, electronic components, and armor are incorporated into the keyboard sections 112 and 114. A minimum of weight is incorporated into the display 410. This configuration ensures that the center of gravity remains over the base for stability. When placed on a flat surface such as a table, this configuration remains stable against tipping even when the display is extended beyond the base to a position closer to the user.

The display is connected through double-acting hinges 412 and 414 to a display support 610. Link mechanisms 612 and 614 connect the display support 610 to the keyboard section 114.

The bottom of the first link mechanism 612 is attached to the rear portion of the keyboard section 114. A pivot 616 connects a first link 620 to the keyboard section 114. A pin 624 at the end of a second link 622 slides within a slot 626. Links 620 and 622 are pivotally attached to each other and to a sequence of pair of links which, in turn, are similarly pivotally attached to each other. A top pair of links 628 and 630 is attached to the display support 610. Link 630 is attached to a pin 632 which slides within a slot 634. Link 628 is attached through a pivot 636. An adjustable stop 638 determines an angle 640 of link 628 with respect to the display support 610. This configuration of links within link mechanism 612 maintains a parallel relationship between components within the link mechanism 612 and between the keyboard section 114 and the display support 610. This ensures that the display support 610 remains horizontal throughout the adjustment of the height of the display 410.

The bottom of the second link mechanism 614 is attached to the end portion of the keyboard section 114. A first link 644 is attached to the keyboard section 114 through a pivot 644. A second link is attached to the first link 644 through a pivot 645. An adjustable stop 648 determines a relative angle 650 between links 642 and 646. A sequence of pairs of links attach link 642 and 646 to top link 652. Link 652 is attached to display support 610 through pivot 654.

Figure 23:
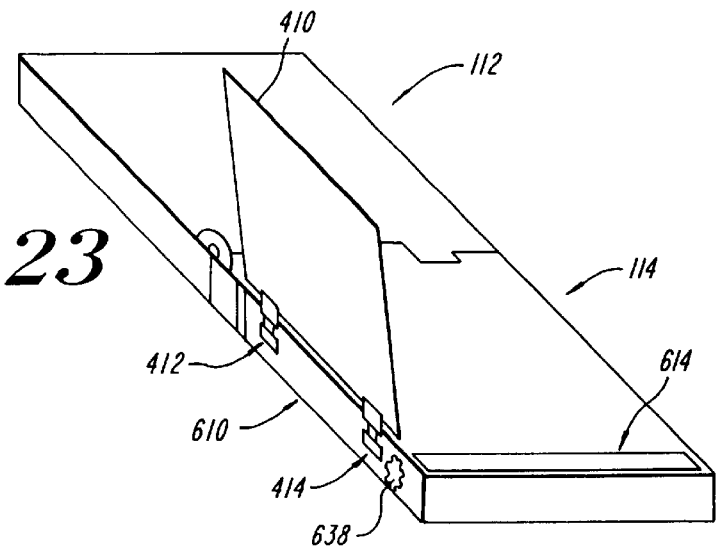
FIG. 23 shows the compact computing device with the link mechanisms in the collapsed condition.

FIG. 23 shows the device with the link mechanisms 612 and 614 in the collapsed condition. In this condition, the display support 610 is stored in the rear portion of the keyboard section 114 behind the collapsed link mechanism 612. The link mechanism 614 is stored in the end portion of the keyboard section 114. From this configuration, the device may be folded to any of the configurations shown in FIGS. 9 through 20.

Figure 24:
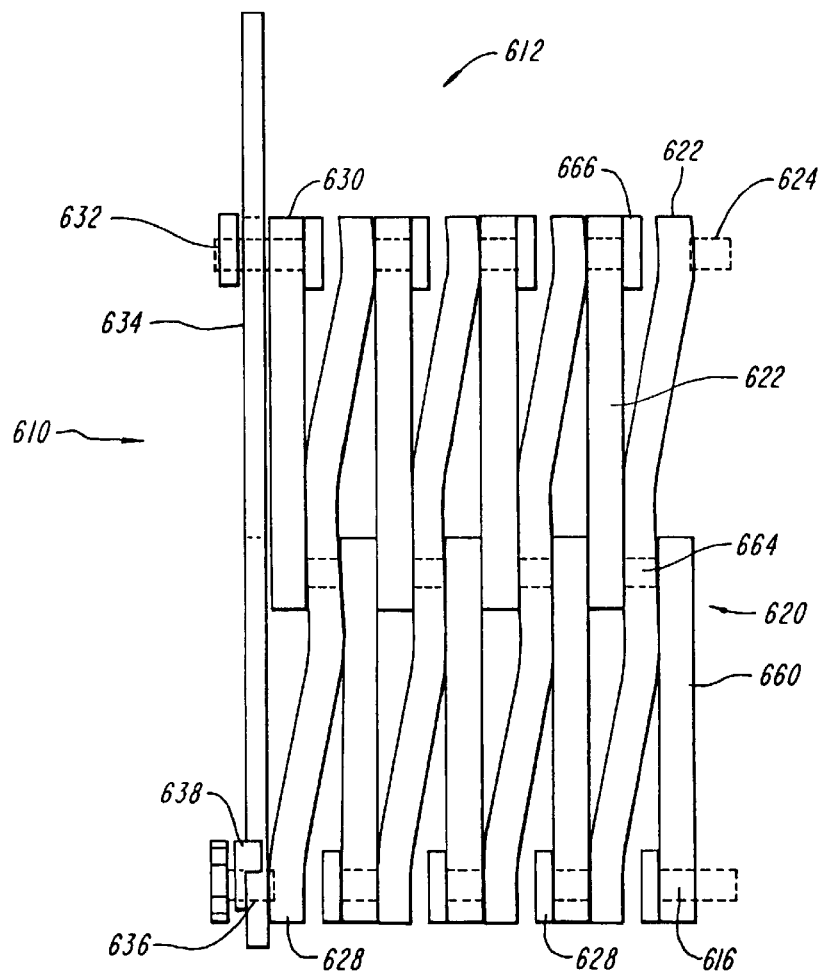
FIG. 24 (not to scale) details a horizontally stacked link mechanism. The thickness is exaggerated to show detail.

Link mechanism 612 is detailed in the top view shown in FIG. 24. The thickness of the links is exaggerated to show detail. Each link is a beam member. The links are arranged in pairs consisting of a curved link such as link 622 and a crank-shaped link such as link 620. The crank-shaped link has two flat sections 660 and 662 connected by a pivot shaft 664 which passes through a circular hole at the center of the curved link 622. The end of the crank-shaped link 620 is connected through a pivot pin 666 to the end of the next curved link. The end of the curved link 622 is connected through a pivot pin 668 to the end of the next crank-shaped link. An arbitrary number of pairs of links can be stacked in this manner and can be stored in this flat horizontal storage position.

Typical dimensions of the links are 1mm thick×10mm high×150mm long. Typically, 4 pairs of links are used. The resultant dimension of the mechanism in the horizontal storage position 12 mm thick×10 mm high×150 mm long. This mechanism can extend to a maximum length of approximately 500 mm. Thus, the collapsible mechanism can be stored within a folded compact computing device and extend to a length considerably greater than any dimension of the folded computing device.

The front end of link mechanism 612 is attached to the keyboard section 114 (shown in FIG. 22). The far end of link 622 is connected to a pin 624 which slides in a slot in the keyboard section 114. The far end of link 620 is connected to a pin 624 which pivots in a hole in the keyboard section 114.

The rear end of link mechanism 612 is attached to the display support 610. The far end of link 628 is connected to a pin 636 which pivots in a hole in the display support 610. The far end of link 630 is connected to a pin 632 which slides in a slot 634 in the display support 610.

The portion of link 630 above its pivot 631 may be shorter than the portion of link 628 above its pivot 631. The portion of link 622 below its pivot 621 may be shorter than the portion of link 620 below its pivot 621. This results in a tilting of link mechanism 612 in the extended position, and the centering of the display with respect to the keyboard sections.

FIG. 25 shows a top view of link mechanism 614 in the storage position. The vertical stacking provides a path for routing wires 670 which carry power and display signals from the keyboard section 114 to the display 410.

FIG. 26 shows a side view of link mechanism 614 in the storage position. Link mechanism 614 is formed from a series of pairs of links such as outer link 642 and inner link 646. A pivot pin such as pin 645 connects the center of each outer link to its corresponding inner link. A pivot pin at each end of each outer link connect the outer link to an inner link from an adjacent pair. Typically 5 pairs of links are used.

The bottom end of the link mechanism 614 is connected to front portion of the end of keyboard section 114 through pivot pin 644. The top end of the link mechanism 614 is connected to the display support 610 through pin 654.

An adjustable stop 648 defines an adjustment angle of link 642 with respect to link 646. A spring 672 acts to counterbalance the weight of the link mechanism 614 and the display 410.

Each link is approximately 10 mm wide×4 mm high×110 mm long. In the collapsed condition the stack has dimensions of approximately 10 mm×20 mm×110 mm. In the extended condition link mechanism 614 is approximately 500 mm long.

The horizontal stacking of mechanism 612 uses less space in the vertical (z) direction than the vertical stacking of mechanism 614. The horizontal stacking is therefore used in the rear hinge to minimize the vertical height of the collapsed link mechanism so that the display can fold over the link mechanism when the display is stored between the keyboard sections in the collapsed condition. In the collapsed condition space is provided for movement of the display support in the vertical direction (toward the keyboard sections) for additional cushioning of the display.

In some embodiments the link mechanisms are constructed of a metal, and the wires are contained within recesses and passages within these metal components. These passages may form a Faraday cage to shield the display signal from electro-magnetic interference (EMI). One of the metal link mechanisms may also be used as an antenna for communications via a cellular modem or wireless ethernet PC card.

In some embodiments the CPU, memory, mass storage, video drivers, and PCMCIA slots are incorporated into keyboard section 114. The batteries are incorporated into keyboard section 112. With this arrangement only the power and the keyboard key switch signals need to cross the keyboard division. These signals are of low frequency and are not susceptible to EMI. The need for special sheilding of these wires is obviated.

SUPPORT AND RIGIDITY OF THE LINK MECHANISMS

In discussing support and rigidity, a set of axes is chosen to coincide with the corner of the display 410 as shown in FIG. 22. The x direction is oriented toward the user, the y is oriented toward the center of the keyboard, and the z axis is oriented vertically upward.

The link mechanism must support the display in an extended position against movement and vibration in an x, y, and z direction. It must also support the display against rotation and rotational vibration about the x, y, and z axes.

The adjustable stop 638 maintains link mechanism 612 in a fixed length. This rigid mechanism maintains a fixed elevation of display against movement in the z-direction.

The location of the end of link 620 is fixed by pivot 616. The slot 626 constrains movement of link 622 and prevents rotation of mechanism 612 about the pivot 616. This combination prevents movement of the display in the y-direction.

The adjustable stop 645 fixed the length of mechanism 614. This prevents tilting of mechanism 612 in the x-direction and prevents movement of the display in the x-direction.

The link mechanism 612 maintains a parallel relationship between the (stationary) keyboard sections and the and the display support. This prevents movement of the display about the x-axis.

Rotation of the display about the y-axis is associated with bending of the link mechanism 612. The stiffness of link mechanism 612 against this bending mode is limited by the limited thickness (approximately 1 mm) of the links in mechanism 612. Further protection against rotation about the y-axis may be realized by connecting the stop 638 directly between the pivoting components consisting of the display 410 and the link 652. In this manner the considerable stiffness of link mechanism 614 against rotation about the y-axis is employed.

Rotation of the display about the z-axis is constrained by link mechanisms 612 and 614. Because the z-axis is oriented parallel to the gravitational force vector, there is little excitation of this mode and little tendency for rotation and rotational vibration about the z-axis.

Counterbalance springs may be incorporated into the adjustable stops 638 and 648. Alternately, torque may be applied by springs incorporated into the keyboard section 114.

Movement of the display in the x direction corresponds to movement closer to the users eyes. This adjustment is effected by compression of link mechanism 114. The pins 616 and 624 may allow a small amount of rotation about the y-axis to allow link mechanism 612 to tilt forward in the x direction toward the user.

DETAILED DESCRIPTION OF THE CUSHIONING SHOWN IN FIG. 27

While the device is in the collapsed condition shown in FIG. 9, the configuration of the display 410, the keyboard sections 112 and 114, and the link mechanisms 612 and 614 should allow movement of the display 410 with respect to the keyboard members 112 and 114. This allows a stiff, brittle display 410 to remain planar even with bendable keyboard sections 112 and 114.

Further cushioning can be realized against impact by configuring the hinges 418 and 424 and link mechanisms 612 and 614 to allow translation in addition to rotation. In the closed position, sufficient clearance is allowed so that the link mechanisms 612 and 614 can move such that the display 410 can move within the key travel region toward each keyboard section 112 and 114.

Figure 27:
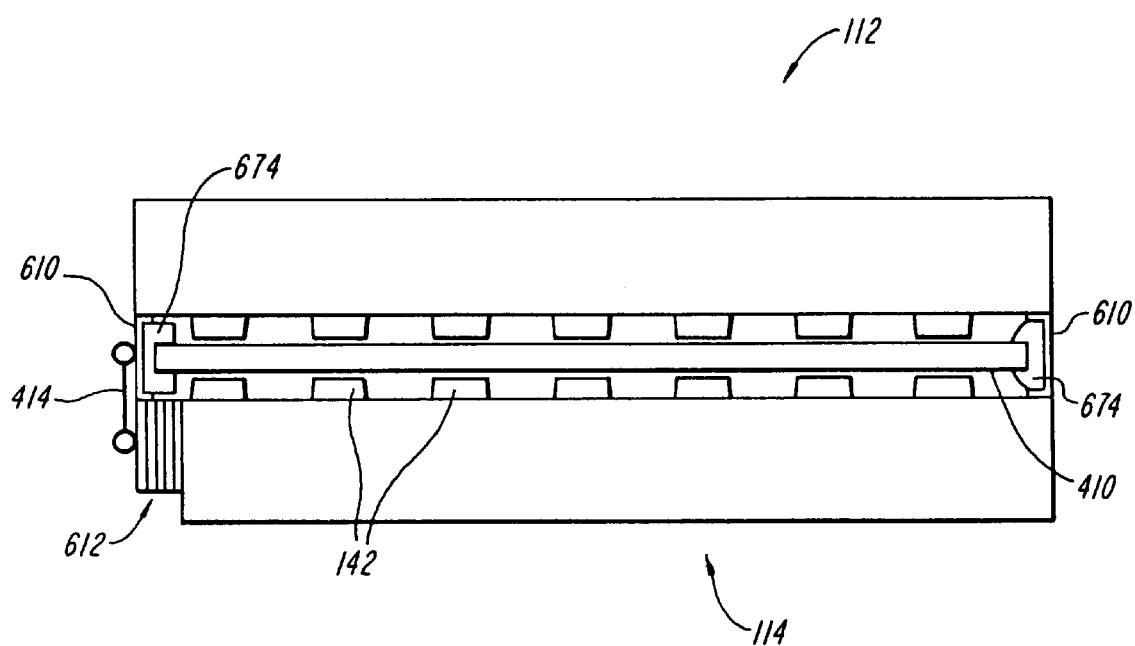
FIG. 27 shows the cushioning of the display support and the display.

Alternately, FIG. 27 shows an elastomeric mount 674 between the display support 610 and the display 410. This elastomeric support may allow translation of the portion of the display proximate to the display support 610 toward each keyboard section 112 and 114 when the device is in the collapsed condition. In addition, this elastomeric support may provide damping of vibrations of the display 410 relative to the keyboard section 114. The damping of these vibrations is particularly important when the link mechanisms 612 and 614 are in the extended position.

In FIG. 27 the display support 610 and elastomeric mount 674 extend to the top portion of the display 410. In this collapsed configuration the display support 610 acts as a shroud to cover the gap between front portions of the keyboard components 112 and 114.

A feature of this design is cushioning distributed over the area of the display 410. The resilience of the individual keys 142 shown in FIG. 1A can act to apply a distributed force needed to accelerate/decelerate the display 410 when the keyboard sections 112 and 114 are accelerated/decelerated due to, for example, dropping the device. This minimizes the bending load applied to the display 410 due to impact.

In an optimal design the device has a closed position wherein there is a resting position in which the display 410 is normally spaced from the keytop surfaces 148 and 150 to avoid routine and unnecessary scratching and wear of the surfaces of the display 410. However, when bending, shock, or impact is imparted to the device, the display 410 (or portions of the display 410) can cross over the keytop surfaces 148 and/or 150. When this happens, forces are applied to those portions of the display 410 which cross over the keytop surfaces 148 and 150. This force tends to cushion the display 410 and tends to accelerate the display 410 away from the depressed keys 142 and back toward its resting position.

The keys on a standard keyboard are movable and have a restoring force to provide tactile feedback as to whether the key has been depressed. This force is typically provided by an elastomeric member of the key. This force can be exploited as above to cushion the display.

This force of the key against the finger is a nonlinear function of key displacement. The force first increases with displacement up to a threshold, then decreases. Thus, once the threshold is passed, the lowered resisting force of the key tends to allow the key to move all the way to the end of its travel. This is to provide the user with clear tactile feedback as to whether the key was pushed or not pushed.

When the key is also used for cushioning the display 410, the display 410 can be protected from shocks of higher magnitude by modifying the nonlinear resilience of the key. The key can be allowed to move in a hyperextended range of key travel beyond the range of a normal keystroke. The spring constant in this hyperextended travel range should be significantly higher than that in the normal range of travel, so that large forces can be applied for large impacts without the requirement of correspondingly large additional key displacement in the hyperextended range.

This protection and cushioning of the display 410 reduces the need for the protective armor typically surrounding laptop computer displays. The display 410 may be an unprotected glass panel, may have a thinner protection than a laptop, or may be protected only around its perimeter, such as by the display support 610 in FIG. 27.

The foregoing discussion should be understood as illustrative and should not be considered to be limiting in any sense. While this invention has been particularly shown and described with references to embodiments thereof, it will be understood by those skilled in the art that various changes in form and details may be made therein without departing from the spirit and scope of the invention as defined by the claims.

Having described the invention, what is claimed is:

1. A device for portable electronic computing, including:
   a) a first keyboard section, said first keyboard section having a first top surface and a plurality of keys protruding from said first top surface,
   b) a second keyboard section, said second keyboard section having a second top surface and a plurality of keys protruding from said second top surface,
   c) a first hinge attached to each of said first and second keyboard sections, said first hinge having a first axis of rotation with respect to said first keyboard section,
   d) a second hinge, said second hinge attached to said first keyboard section, said second hinge having an axis of rotation with respect to said first keyboard section perpendicular to said first axis of said first hinge,
   e) a third hinge, said third and hinge attached to said first keyboard section, said third hinge having an axis of rotation with respect to said first keyboard section perpendicular to said first axis of said first hinge, and,
   f) a substantially planar display having a front surface for display of information from a digital computer and a rear surface, said display pivotally connected to said first keyboard section through said second hinge and said third hinge,
   whereby through a sequence of pivoting actions around said first and second axes, said display can pivot about said first axis such that its front surface faces said first top surface, and said second keyboard section can pivot about said second perpendicular second axis such that said second top surface faces said display rear surface such that said device forms a collapsed condition in which said display is sandwiched between said first and second keyboard sections.

2. The device of claim 1, wherein:
   said second and third hinges share a common axis of rotation.

3. The device of claim 2, wherein:
   said common axis of rotation is perpendicular to said first axis of rotation.

4. The device of claim 1, further comprising:
   a fourth hinge attached to each of said first and second keyboard sections.

5. The device of claim 4, wherein:
   said first and fourth hinges share a common axis of rotation.

* * * * *